(12) United States Patent
Chudzik et al.

(10) Patent No.: US 7,008,667 B2
(45) Date of Patent: Mar. 7, 2006

(54) BIOACTIVE AGENT RELEASE COATING

(75) Inventors: Stephen J. Chudzik, St. Paul, MN (US); Aron B. Anderson, Minnetonka, MN (US); Ralph A. Chappa, Prior Lake, MN (US); Timothy M. Kloke, Eden Prairie, MN (US)

(73) Assignee: SurModics, Inc., Eden Prairie, MN (US)

( * ) Notice: Subject to any disclaimer, the term of this patent is extended or adjusted under 35 U.S.C. 154(b) by 28 days.

(21) Appl. No.: 10/268,163

(22) Filed: Oct. 10, 2002

(65) Prior Publication Data

US 2003/0031780 A1 Feb. 13, 2003

Related U.S. Application Data

(60) Continuation of application No. 09/989,033, filed on Nov. 21, 2001, now Pat. No. 6,890,583, which is a division of application No. 09/693,771, filed on Oct. 20, 2000, now Pat. No. 6,344,035, which is a division of application No. 09/292,510, filed on May 15, 1999, now Pat. No. 6,214,901.

(60) Provisional application No. 60/083,135, filed on Apr. 27, 1998.

(51) Int. Cl.
*B05D 3/00* (2006.01)
*A61K 9/14* (2006.01)

(52) U.S. Cl. ...................... 427/2.1; 424/489

(58) Field of Classification Search ........... 424/489; 427/2.1

See application file for complete search history.

(56) References Cited

U.S. PATENT DOCUMENTS

| 4,069,307 A | 1/1978 | Higuchi et al. |
| 4,292,965 A | 10/1981 | Nash et al. |
| 4,391,797 A | 7/1983 | Folkman |
| 4,603,152 A * | 7/1986 | Laurin et al. ............... 604/265 |
| 4,623,346 A | 11/1986 | von Bittera et al. |
| 4,627,852 A | 12/1986 | von Bittera et al. |
| 4,722,906 A | 2/1988 | Guire |
| 4,768,507 A | 9/1988 | Fischell et al. |

(Continued)

FOREIGN PATENT DOCUMENTS

EP 0 294 905 A1 12/1988

(Continued)

OTHER PUBLICATIONS

Virmani, R., MD et al., "Mechanism of Late In-Stent Restenosis After Implantation of a Paclitaxel Derivate-Eluting Polymer Stent System in Humans", Circulation, 2002; 106: 2649-2651.

(Continued)

*Primary Examiner*—Thurman K Page
*Assistant Examiner*—Humera N. Sheikh
(74) *Attorney, Agent, or Firm*—Fredrikson & Byron, P.A.

(57) ABSTRACT

A coating composition for use in coating implantable medical devices to improve their ability to release bioactive agents in vivo. The coating composition is particularly adapted for use with devices that undergo significant flexion and/or expansion in the course of their delivery and/or use, such as stents and catheters. The composition includes the bioactive agent in combination with a mixture of a first polymer component such as poly(butyl methacrylate) and a second polymer component such as poly(ethylene-co-vinyl acetate).

27 Claims, 1 Drawing Sheet

U.S. PATENT DOCUMENTS

| | | |
|---|---|---|
| 4,826,759 A | 5/1989 | Guire |
| 4,916,193 A | 4/1990 | Tang et al. |
| 4,959,217 A | 9/1990 | Sanders et al. |
| 4,973,493 A | 11/1990 | Guire |
| 4,979,959 A | 12/1990 | Guire |
| 4,994,071 A | 2/1991 | MacGregor |
| 5,002,582 A | 3/1991 | Guire |
| 5,019,096 A * | 5/1991 | Fox et al. ............... 600/36 |
| 5,114,719 A | 5/1992 | Sabel et al. |
| 5,165,952 A | 11/1992 | Solomon et al. |
| 5,180,366 A | 1/1993 | Woods |
| 5,217,492 A | 6/1993 | Guire |
| 5,221,698 A | 6/1993 | Amiden et al. |
| 5,258,041 A | 11/1993 | Guire |
| 5,263,992 A | 11/1993 | Guire |
| 5,304,121 A | 4/1994 | Sahatjian |
| 5,310,559 A | 5/1994 | Shah et al. |
| 5,342,348 A | 8/1994 | Kaplan |
| 5,356,433 A | 10/1994 | Rowland et al. |
| 5,380,299 A | 1/1995 | Fearnot et al. |
| 5,414,075 A | 5/1995 | Swan |
| 5,419,760 A | 5/1995 | Narciso et al. |
| 5,437,656 A | 8/1995 | Shikani et al. |
| 5,443,505 A | 8/1995 | Wong et al. |
| 5,447,724 A | 9/1995 | Helmus et al. |
| 5,449,382 A | 9/1995 | Dayton |
| 5,451,424 A | 9/1995 | Solomon et al. |
| 5,464,650 A | 11/1995 | Berg et al. |
| 5,466,233 A | 11/1995 | Weiner |
| 5,512,055 A | 4/1996 | Domb et al. |
| 5,512,329 A | 4/1996 | Guire |
| 5,525,348 A | 6/1996 | Whitbourne |
| 5,545,208 A | 8/1996 | Wolff et al. |
| 5,563,056 A | 10/1996 | Swan |
| 5,567,417 A | 10/1996 | Sasisekharan et al. |
| 5,569,463 A | 10/1996 | Helmus et al. |
| 5,578,075 A | 11/1996 | Dayton |
| 5,591,227 A | 1/1997 | Dinh et al. |
| 5,605,696 A | 2/1997 | Eury et al. |
| 5,609,629 A * | 3/1997 | Fearnot et al. ............ 623/1.42 |
| 5,624,411 A | 4/1997 | Tuch |
| 5,624,975 A | 4/1997 | Valencia |
| 5,637,113 A | 6/1997 | Tartaglia et al. |
| 5,637,460 A | 6/1997 | Swan |
| 5,651,968 A | 7/1997 | Good |
| 5,651,986 A | 7/1997 | Brem et al. |
| 5,656,286 A | 8/1997 | Miranda et al. |
| 5,674,241 A | 10/1997 | Bley et al. |
| 5,714,360 A | 2/1998 | Swan |
| 5,741,551 A | 4/1998 | Guire |
| 5,744,515 A | 4/1998 | Clapper |
| 5,766,242 A | 6/1998 | Wong et al. |
| 5,773,019 A | 6/1998 | Ashton |
| 5,783,502 A | 7/1998 | Swanson |
| 5,824,049 A | 10/1998 | Ragheb et al. |
| 5,824,072 A | 10/1998 | Wong |
| 5,837,313 A | 11/1998 | Ding et al. |
| 5,858,653 A | 1/1999 | Duran |
| 5,877,224 A * | 3/1999 | Brocchini et al. ....... 514/772.2 |
| 5,879,697 A | 3/1999 | Ding et al. |
| 5,886,026 A | 3/1999 | Hunter |
| 5,895,407 A | 4/1999 | Jayaraman |
| 5,897,911 A | 4/1999 | Loeffler |
| 5,899,935 A | 5/1999 | Ding |
| 5,902,475 A | 5/1999 | Trozera |
| 5,942,555 A | 8/1999 | Swanson |
| 5,951,586 A | 9/1999 | Berg |
| 5,980,972 A | 11/1999 | Ding |
| 5,981,298 A | 11/1999 | Chudzik |
| 5,997,517 A | 12/1999 | Whitbourne |
| 6,001,386 A | 12/1999 | Ashton |
| 6,007,833 A | 12/1999 | Chudzik |
| 6,013,099 A | 1/2000 | Dinh |
| 6,077,698 A | 6/2000 | Swan |
| 6,090,995 A | 7/2000 | Reich |
| 6,096,070 A | 8/2000 | Ragheb et al. |
| 6,099,562 A | 8/2000 | Ding et al. |
| 6,110,483 A | 8/2000 | Whitbourne et al. |
| 6,120,536 A | 9/2000 | Ding et al. |
| 6,120,847 A | 9/2000 | Yang et al. |
| 6,121,027 A | 9/2000 | Clapper |
| 6,129,933 A | 10/2000 | Oshlack et al. |
| 6,143,037 A | 11/2000 | Goldstein |
| 6,153,252 A | 11/2000 | Hossainy |
| 6,156,345 A | 12/2000 | Chudzik |
| 6,156,373 A | 12/2000 | Zhong et al. |
| 6,214,901 B1 | 4/2001 | Chudzik et al. |
| 6,217,895 B1 | 4/2001 | Guo |
| 6,235,306 B1 | 5/2001 | Miranda et al. |
| 6,251,136 B1 | 6/2001 | Guruwaiya et al. |
| 6,284,305 B1 | 9/2001 | Ding et al. |
| 6,287,285 B1 | 9/2001 | Michal et al. |
| 6,331,313 B1 | 12/2001 | Wong et al. |
| 6,344,035 B1 | 2/2002 | Chudzik et al. |
| 6,358,556 B1 | 3/2002 | Ding et al. |
| 6,399,704 B1 | 6/2002 | Laurin et al. |
| 6,451,373 B1 | 9/2002 | Hossainy et al. |
| 6,497,691 B1 | 12/2002 | Bevins et al. |
| 6,506,411 B1 | 1/2003 | Hunter |
| 6,544,544 B1 | 4/2003 | Hunter |
| 6,548,078 B1 | 4/2003 | Guo |
| 6,585,764 B1 | 7/2003 | Wright et al. |
| 6,653,426 B1 | 11/2003 | Alvarado et al. |
| 6,682,553 B1 | 1/2004 | Webler, Jr. |
| 2001/0014717 A1 | 8/2001 | Hossainyn et al. |
| 2001/0029351 A1 | 10/2001 | Falotico et al. |
| 2002/0004101 A1 | 1/2002 | Ding et al. |
| 2002/0005206 A1 | 1/2002 | Falotico et al. |
| 2002/0007213 A1 | 1/2002 | Falotico et al. |
| 2002/0007214 A1 | 1/2002 | Falotico et al. |
| 2002/0007215 A1 | 1/2002 | Falotico et al. |
| 2002/0013298 A1 | 1/2002 | Hunter |
| 2002/0018795 A1 | 2/2002 | Whitbourne et al. |
| 2002/0026236 A1 | 2/2002 | Helmus et al. |
| 2002/0032434 A1 | 3/2002 | Chudzik et al. |
| 2002/0032477 A1 | 3/2002 | Helmus et al. |
| 2002/0051730 A1 | 5/2002 | Bodnar Stanko et al. |
| 2002/0051731 A1 | 5/2002 | Bodnar Stanko et al. |
| 2002/0054900 A1 | 5/2002 | Kamath et al. |
| 2002/0055721 A1 | 5/2002 | Palasis |
| 2002/0071902 A1 | 6/2002 | Ding et al. |
| 2002/0091433 A1 | 7/2002 | Ding et al. |
| 2002/0107330 A1 | 8/2002 | Pinchuk et al. |
| 2002/0111590 A1 | 8/2002 | Davila et al. |
| 2002/0120326 A1 | 8/2002 | Michal |
| 2002/0133183 A1 | 9/2002 | Lentz et al. |
| 2002/0138048 A1 | 9/2002 | Tuch |
| 2002/0183380 A1 | 12/2002 | Hunter |
| 2002/0188037 A1 | 12/2002 | Chudzik |
| 2003/0004209 A1 | 1/2003 | Hunter |
| 2003/0039675 A1 | 2/2003 | Kunz |
| 2003/0065377 A1 | 4/2003 | Davila |
| 2003/0083646 A1 | 5/2003 | Sirhan Motasim |
| 2003/0094736 A1 | 5/2003 | Qin |
| 2003/0096131 A1 | 5/2003 | Beavers et al. |
| 2003/0097088 A1 | 5/2003 | Pacetti |
| 2003/0105245 A1 | 6/2003 | Amsden |
| 2003/0157187 A1 | 8/2003 | Hunter |
| 2003/0171496 A1 | 9/2003 | Pinchuk |
| 2003/0175324 A1 | 9/2003 | Robinson et al. |
| 2003/0204168 A1 | 10/2003 | Bosma |
| 2003/0207856 A1 | 11/2003 | Tremble et al. |
| 2003/0232087 A1 | 12/2003 | Lawin |
| 2003/0232122 A1 | 12/2003 | Chappa |

| | | | | | | |
|---|---|---|---|---|---|---|
| 2003/0236513 A1 | 12/2003 | Schwarz et al. | | WO | WO 95/03795 | 2/1995 |
| 2003/0236514 A1 | 12/2003 | Schwarz et al. | | WO | WO 96/03984 | 2/1996 |
| 2004/0022853 A1 | 2/2004 | Ashton | | WO | WO 96/37165 | 11/1996 |
| 2004/0030380 A1 | 2/2004 | Shulze | | WO | WO 96/39821 | 12/1996 |
| 2004/0054104 A1 | 3/2004 | Pacetti | | WO | WO 97/16544 | 5/1997 |
| 2004/0058056 A1 | 3/2004 | Osaki | | WO | WO 97/34935 | 9/1997 |
| 2004/0059408 A1 | 3/2004 | Alvarado | | WO | WO 88/02623 | 4/1998 |
| 2004/0077797 A1 | 4/2004 | Asgarzadeh | | WO | WO 98/17331 | 4/1998 |
| 2004/0086542 A1 | 5/2004 | Hossainy | | WO | WO 99/08717 | 2/1999 |
| 2004/0111144 A1 | 6/2004 | Lawin | | WO | WO 99/16907 | 4/1999 |
| 2004/0117006 A1 | 6/2004 | Lewis | | WO | WO 99/38546 | 8/1999 |
| 2004/0117007 A1 | 6/2004 | Whitbourne | | WO | WO 99/43688 | 9/1999 |
| 2004/0170752 A1 | 9/2004 | Luthra | | WO | WO 99/47129 | 9/1999 |
| 2004/0202691 A1 | 10/2004 | Richard | | WO | WO 99/47176 | 9/1999 |
| 2004/0224001 A1 | 11/2004 | Pacetti | | WO | WO 99/64086 | 12/1999 |
| 2004/0234737 A1 | 11/2004 | Pacetti | | WO | WO 00/12163 | 3/2000 |
| 2004/0243225 A1 | 12/2004 | Ragheb | | WO | WO 00/40593 | 7/2000 |
| 2005/0025802 A1 | 2/2005 | Richard | | WO | WO 00/55396 | 9/2000 |
| 2005/0025830 A1 | 2/2005 | Bruinewoud | | WO | WO 01/21326 | 3/2001 |
| 2005/0037047 A1 | 2/2005 | Song | | WO | WO 01/36008 | 5/2001 |
| 2005/0037048 A1 | 2/2005 | Song | | WO | WO 01/44174 | 6/2001 |
| 2005/0037052 A1 | 2/2005 | Udipi | | WO | WO 01/66161 | 9/2001 |
| 2005/0042293 A1 | 2/2005 | Jackson | | WO | WO 01/87263 | 11/2001 |
| 2005/0064005 A1 | 3/2005 | Dinh | | WO | WO 01/87342 | 11/2001 |
| 2005/0064011 A1 | 3/2005 | Song | | WO | WO 01/87372 | 11/2001 |
| 2005/0064038 A1 | 3/2005 | Dinh | | WO | WO 01/87373 | 11/2001 |
| | | | | WO | WO 01/87374 | 11/2001 |
| FOREIGN PATENT DOCUMENTS | | | | WO | WO 01/87375 | 11/2001 |
| EP | 0 470 569 A1 | 2/1992 | | WO | WO 01/87376 | 11/2001 |
| EP | 0 543 653 A1 | 6/1993 | | WO | WO 02/26139 | 4/2002 |
| EP | 0 551 182 A1 | 7/1993 | | WO | WO 02/26271 | 4/2002 |
| EP | 0 568 310 A1 | 11/1993 | | WO | WO 02/26281 | 4/2002 |
| EP | 0 274 846 B1 | 2/1994 | | WO | WO 03/022323 | 3/2003 |
| EP | 0 604 022 | 6/1994 | | WO | WO 03/064015 | 8/2003 |
| EP | 0 623 354 A1 | 11/1994 | | WO | WO 04/000267 | 12/2003 |
| EP | 0 706 376 | 4/1996 | | | | |
| EP | 0 716 836 | 6/1996 | | | | |
| EP | 0 734 721 | 10/1996 | | | | |
| EP | 0 747 069 | 12/1996 | | | | |
| EP | 0 747 069 | 1/1998 | | | | |
| EP | 0 879 595 | 11/1998 | | | | |
| EP | 0 923 953 A2 | 6/1999 | | | | |
| EP | 0 945 148 | 9/1999 | | | | |
| EP | 1 174 157 | 1/2002 | | | | |
| JP | 2036882 | 2/1990 | | | | |
| JP | 0 8033718 A | 2/1996 | | | | |
| JP | 09099056 A | 4/1997 | | | | |
| JP | 09194347 A | 7/1997 | | | | |
| WO | WO 89/05616 | 6/1989 | | | | |
| WO | WO90/00887 | 2/1990 | | | | |
| WO | WO 90/01969 | 3/1990 | | | | |
| WO | WO 90/13332 | 11/1990 | | | | |
| WO | WO 91/03990 | 4/1991 | | | | |
| WO | WO 91/07154 | 5/1991 | | | | |
| WO | WO 91/10424 | 7/1991 | | | | |
| WO | WO 91/11193 | 8/1991 | | | | |
| WO | WO 91/12779 | 9/1991 | | | | |
| WO | WO 91/12846 | 9/1991 | | | | |
| WO | WO 92/00747 | 1/1992 | | | | |
| WO | WO 92/11895 | 7/1992 | | | | |
| WO | WO 92/12717 | 8/1992 | | | | |
| WO | WO 92/15286 | 9/1992 | | | | |
| WO | WO 93/06792 | 4/1993 | | | | |
| WO | WO 93/11120 | 6/1993 | | | | |
| WO | WO 93/16176 | 8/1993 | | | | |
| WO | WO 93/16687 | 9/1993 | | | | |
| WO | WO 93/17669 | 9/1993 | | | | |
| WO | WO 94/11032 | 5/1994 | | | | |
| WO | WO 94/21308 | 9/1994 | | | | |
| WO | WO 94/21309 | 9/1994 | | | | |
| WO | WO 94/24962 | 11/1994 | | | | |
| WO | WO 95/03036 | 2/1995 | | | | |

OTHER PUBLICATIONS

Grube, E., MD, et al., "Six- and Twelve-Month Results From a Randomized, Double-Blind Trial on a Slow-Release Paclitaxel-Eluting Stent for De Novo Coronary Lesions", Circulation, 2003; 107: 38-42.

Serruys, P., MD, PhD, "Final ACTION results (Actinomycin D) Test", (Sep. 2002).

Trevino, M., "Results for drug-eluting stents disappoint, Diagnostic Imaging Online", (Apr. 25, 2002), http://www.dimag.com/dinews/2002042501.shtml.

Jampel, H. D., MD, et al., "In Vitro Release of Hydrophobic Drugs From Polyanhydride Disks", Ophthalmic Surgery, Nov. 1991, vol. 22, No. 11, pp. 676-680.

Sousa, J. Eduardo, MD, PhD, et al., "Clinical Cardiology: New Frontiers, New Frontiers in Cardiology, Drug-Eluting Stents: Part I", Circulation 2003; 107:2274-2279.

Voisard, R., et al., "Suche nach neuen Strategien zur Verhutung von Restenosen nach Angioplatie: Der Effekt von Cytostakika auf die Migrationfahigkeit von restenosierenden Plaquezellen des Menschen in vitro", Vasa Suppl. 1992; 35:132-33.

Hermans, W.R. M., MD, et al., Prevention of restenosis after percutaneous transluminal coronary angioplasty: The search for a "magic bullet", Am. Heart Journal, vol. 122, No. 1, pt. 1, 171-187, (1990).

O'Keefe, Jr., J., MD, et al., "Ineffectiveness of Colchicine for the Prevention of Restenosis After Coronary Angioplasty", JACC, vol. 19, No. 7, Jun. 1992: 1597-1600.

Hirata, S., et al., Inhibition of In Vitro Vascular Endothelial Cell Proliferation and In Vivo Neovascularization by Low-dose Methotrexate, *Arthritis and Rheumatism*, vol. 32, No. 9 (Sep. 1989), p. 1065-1073.

Coronary Artery Disease, vol. 3, No. 3, (Mar. 1992), pp. 237-248.

Lambert, T., et al., "A New Method for Arterial Drug Delivery via Removable Stent", *JACC* vol. 21 No. 2, 834-2, (Feb. 1993).

Cox, D., MD, et al., "Effect of local delivery of heparin and methotrexate on neointimal proliferation in stented porcine coronary arteries", Coronary Artery Disease, Mar. 1992: vol. 3, No. 3, pp. 237-248.

Pitt, C.G., et al., "Progress in Contraceptive Delivery Systems", (Hafez, E.S.E, van Os, W., editors, vol. 1, pp. 17-18, MTP Press, Lancaster (1980).

Bartoli, M., et al., "In vitro and in vivo antitumoral activity of free, and encapsulated taxol", *J. Microencapsulation*, vol. 7, No. 2, 191-197 (1990).

The 2nd International Coronary Stenting Summit, Mar. 1-2, 1991.

Cox, David A., et al., "Local Delivery of Heparin and Methotrexate Fails to Inhibit In Vivo Smooth Muscle Cell Proliferation, *Supplement to Circulation*, Abstracts from the 64th Scientific Sessions," vol. 84, No. 4, Oct. 1991.

Dev, Vishva, et al., Kinetics of Drug Delivery to the Arterial Wall Via Polyurethane Coated Removable Nitinol Stent-Comparative Study of 2 Drugs, Cedars-Sinai Medical Center, Los Angeles, CA., *Circulation*, vol. 88, No. 4, Part 2, Oct. 1993.

Lambert, Thomas, et al., Localized Arterial Drug Delivery from a Polymer Coated Removable Metallic Stent: Kinetics and Bioactivity of Forskolin, Cedars-Sinai Medical Center, Los Angeles, CA., *Circulation*, vol. 88, No. 4, Part 2, Oct. 1993.

Sasabe et al., "Dielectric Relaxations and Electrical Conductivities of Poly(alkyl Methacrylates) under High Pressure", J. Polymer science 6 (1968) pp. 1401-1418.

Brown LR, Edelman ER, Fischel-Ghodsian F, Langer R, Characterization of glucose-mediate insulin release from implantable polymers, Pharm Sci 1996 Dec; 85 (12): 1341-5.

Catz P, Friend DR, In vitro evaluations of transdermal levonorgestrel, Drug Des Deliv, 1990, May; 6 (1): 49-60.

Edelman ER, Simons M, Sirois MG, Rosenberg RD, c-myc in vasculoproliferative disease, Circ Res 1995 Feb; 76(2): 176-82.

Eliaz R, Wallach D, Kost J, Long-term protection against the effects of tumor necrosis factor by controlled delivery of the soluble p55 TNF receptor, Cytokine, 1996, Jun.; 8(6): 482-7.

Flemmig TF, Weinacht S. Rudiger S, Rumetsch M, Jung A, klaiber B, Adjunctive controlled topical application of tetracycline HCI in the treatment of localized persistent or recurrent periodontitis. Effects on clinical parameters and elastase-alphal-proteinase inhibitor in gingival crevicular fluid, J Chin Periodontol Oct.; 23 1996 (10):914-21.

Folkman J. How the field of controlled release technology began, and its central role in the development of angiogenesis research, Biomaterials, 1990, Nov.; 11 (9): 615-8.

Friling R, Yassur Y, Levy R, Kost J. Schwartz B, Mikhailowsky R, Lamprecht SA, A role of transforming growth factor-beta 1 in the control of corneal neovascularization, In Vivo 10, 59-64 (1996).

Goodson JM, Hogan PE, Dunham SL, Clinical responses following periodontal treatment by local drug delivery, J Periodontal Nov.; 1985 56 (11 Suppl): 81-7.

Huland E, Falk B, Hubner D, Huland H, In vivo system to detect long-term continuous release of bioactive interleukin-2 by immunopharmacological depot preparations in nude mice with human tumors, Int. J. Cancer, 1995, 62, 605-9.

Lees VC, Fan TP, West DC, Angiogenesis in a delayed revascularization model is accelerated by angiogenic oligosaccharides of hyaluronan, Lab Invest, 1995, 73, 259-66.

Lesser GJ, Grossman SA, Leong KW, et al., In vitro and in vivo studies of subcutaneous hydromorphone implants designed for the treatment of cancer pain, Pain, 1996, May-Jun.; 65 (2-3): 265-72.

Lopez JJ, Edelman ER, Stamler A, et al., Angiogenic potential of perivascularly delivered aFGF in a porcine model of chronic myocardial ischemia, Am J Physiol 1998 Mar.; 274 (3 Pt 2): H930.

Ozaki H. Hayashi H, Vinores SA, Moromizato Y, Campochiaro PA, Oshima K, Intravitreal sustained release of VEGF causes retinal neovascularization in rabbits and breakdown of the blood-retinal barrier in rabbits and primates, Exp Eye Res, 1997, 64, 505-17.

Sellke FW, Li J, Stamler A, Lopez JJ, Thomas KA, Simons M, Angiogenesis induced by acidic fibroblast growth factor as an alternative method of revascularization for chronic myocardial ischemia, Surgery 1996 Aug.; 120 (2): 182-8.

Suzuki, T. et al. Stent-based delivery of sivolimus release. Circulation 2001, 104: 1188-1193.

Jafary, F, et al Point-Counterpoint: Drug Eluting Stent Euphoria (2002) (Medscape from WEBMD).

Morice eet al, A Rondomized Comparison of a Sirolimus-Eluting Stent, N Engl J Med, Jun.; 2002 346, 1773-1780.

Raman et al, Coated Stents: Local Pharmacology, Semin Intervent Cardiol 1998: 3: 133-137.

Whelan et al, Mechanisms of Drug Loading and Release Kinetics, Semin Intervent Cardiol 1998; 3: 127-131.

Klugherz et al, Twenty-eight-day Efficacy and Phamacokinetics, Coronary Artery Disease 2002 13 (3).

Regar et al, Stent Development and Local Drug Delivery, British Med Bulletin 2001; 59: 227-48.

Serruys et al., Rapamycin Eluting Stent: the Onset of a New Era in Interventional Cardiology, Heart 2002 (87) 305-307.

Catz P, Friend DR, In vitro evaluations of transdermal levonorgestrel, Drug Des Deliv, 1990, May; 6 (1): 49-60.

Edelman ER, Simons M., Sirois MG, Rosenberg RD, c-myc in vasculoproliferative disease, Circ Res 1995 Feb.; 76(2): 176-82.

Eliaz R, Wallach D, Kost J. Long-term protection against the effects of tumor necrosis factor by controlled delivery of the soluble p55 TNF receptor, Cytokine, 1996, Jun.; 8(6): 482-7.

Flemmig TF, Weinacht S, Rudiger S, Rumetsch M, Jung A, Klaiber B, Adjunctive controlled topical application of tetracycline HCI in the treatment of localized persistent or recurrent periodontitis. Effects on clinical parameters and elastase-alphal-proteinase inhibitor in gingival crevicular fluid, J Chin Periodontol 1996 Oct., 23 (10):914-21.

Folkman J, How the field of controllled-release technology began, and its central role in the development of angiogenesis research, Biomaterials, 1990, Nov.; 11 (9): 615-8.

Friling R, Yassur Y, Levy R, Kost J. Schwartz B, Mikhailowsky R, Lamprecht SA, A role of transforming growth factor-beta 1 in the control of corneal neovascularization, In Vivo 10, 59-64 (1996).

Klugherz et al, Twenty-eight day Efficacy and Pharmacokinetics, Coronary Artery Disease 2002 13 (3).

* cited by examiner

BIOACTIVE AGENT RELEASE COATING

CROSS REFERENCE TO RELATED APPLICATIONS

The present application is a continuation of U.S. patent application filed Nov. 21, 2001 and assigned Ser. No. 09/989,033 now U.S. Pat. No. 6,890,583, which is a divisional of U.S. patent application filed Oct. 20, 2000 and assigned Ser. No. 09/693,771 (now U.S. Pat. No. 6,344,035, issued Feb. 5, 2002), which is a divisional of U.S. patent application filed Apr. 15, 1999 and assigned Ser. No. 09/292,510 (now U.S. Pat. No. 6,214,901, issued Apr. 10, 2001), which is a continuation-in-part of provisional U.S. patent application filed Apr. 27, 1998 and assigned Ser. No. 60/083,135, the entire disclosure of which is incorporated herein by reference.

TECHNICAL FIELD

In one aspect, the present invention relates to a process of treating implantable medical devices with coating compositions to provide the release of pharmaceutical agents from the surface of the devices under physiological conditions. In another aspect, the invention relates to the coating compositions, per se, and to devices coated with such compositions.

BACKGROUND OF THE INVENTION

Many surgical interventions require the placement of a medical device into the body. While necessary and beneficial for treating a variety of medical conditions, the placement of metal or polymeric devices in the body gives rise to numerous complications. Some of these complications include: increased risk of infection; initiation of a foreign body response resulting in inflammation and fibrous encapsulation; and initiation of a wound healing response resulting in hyperplasia and restenosis. These, and other complications must be dealt with when introducing a metal or polymeric device into the body.

One approach to reducing the potential harmful effects of such an introduction is to attempt to provide a more biocompatible implantable device. While there are several methods available to improve the biocompatibility of implantable devices, one method which has met with limited success is to provide the device with the ability to deliver bioactive compounds to the vicinity of the implant. By so doing, some of the harmful effects associated with the implantation of medical devices can be diminished. Thus, for example, antibiotics can be released from the surface of the device to minimize the possibility of infection, and anti-proliferative drugs can be released to inhibit hyperplasia. Another benefit to the local release of bioactive agents is the avoidance of toxic concentrations of drugs which are sometimes necessary, when given systemically, to achieve therapeutic concentrations at the site where they are needed.

Although the potential benefits expected from the use of medical devices capable of releasing pharmaceutical agents from their surfaces is great, the development of such medical devices has been slow. This development has been hampered by the many challenges that need to be successfully overcome when undertaking said development. Some of these challenges are: 1) the requirement, in some instances, for long term release of bioactive agents; 2) the need for a biocompatible, non-inflammatory device surface; 3) the need for significant durability, particularly with devices that undergo flexion and/or expansion when being implanted or used in the body; 4) concerns regarding processability, to enable the device to be manufactured in an economically viable and reproducible manner; and 5) the requirement that the finished device be sterilizable using conventional methods.

Several implantable medical devices capable of delivering medicinal agents have been described. Several patents are directed to devices utilizing biodegradable or bioresorbable polymers as drug containing and releasing coatings, including Tang et al, U.S. Pat. No. 4,916,193 and MacGregor, U.S. Pat. No. 4,994,071. Other patents are directed to the formation of a drug containing hydrogel on the surface of an implantable medical device, these include Amiden et al, U.S. Pat. No. 5,221,698 and Sahatjian, U.S. Pat. No. 5,304,121. Still other patents describe methods for preparing coated intravascular stents via application of polymer solutions containing dispersed therapeutic material to the stent surface followed by evaporation of the solvent. This method is described in Berg et al, U.S. Pat. No. 5,464,650.

However, there remain significant problems to be overcome in order to provide a therapeutically significant amount of a bioactive compound on the surface of the implantable medical device. This is particularly true when the coating composition must be kept on the device in the course of flexion and/or expansion of the device during implantation or use. It is also desirable to have a facile and easily processable method of controlling the rate of bioactive release from the surface of the device.

Although a variety of hydrophobic polymers have previously been described for use as drug release coatings, Applicant has found that only a small number possess the physical characteristics that would render them useful for implantable medical devices which undergo flexion and/or expansion upon implantation. Many polymers which demonstrate good drug release characteristics, when used alone as drug delivery vehicles, provide coatings that are too brittle to be used on devices which undergo flexion and/or expansion. Other polymers can provoke an inflammatory response when implanted. These or other polymers demonstrate good drug release characteristics for one drug but very poor characteristics for another.

Some polymers show good durability and flexibility characteristics when applied to devices without drug, but lose these favorable characteristics when drug is added. Furthermore, often times the higher the concentration of drugs or the thicker the application of polymer to the device surface, the poorer the physical characteristics of the polymer become. It has been very difficult to identify a polymer which provides the proper physical characteristics in the presence of drugs and one in which the drug delivery rate can be controlled by altering the concentration of the drug in the polymer or the thickness of the polymer layer.

There remains a need, therefore, for an implantable medical device that can undergo flexion and/or expansion upon implantation, and that is also capable of delivering a therapeutically significant amount of a pharmaceutical agent or agents from the surface of the device.

SUMMARY OF THE INVENTION

Figure 1:
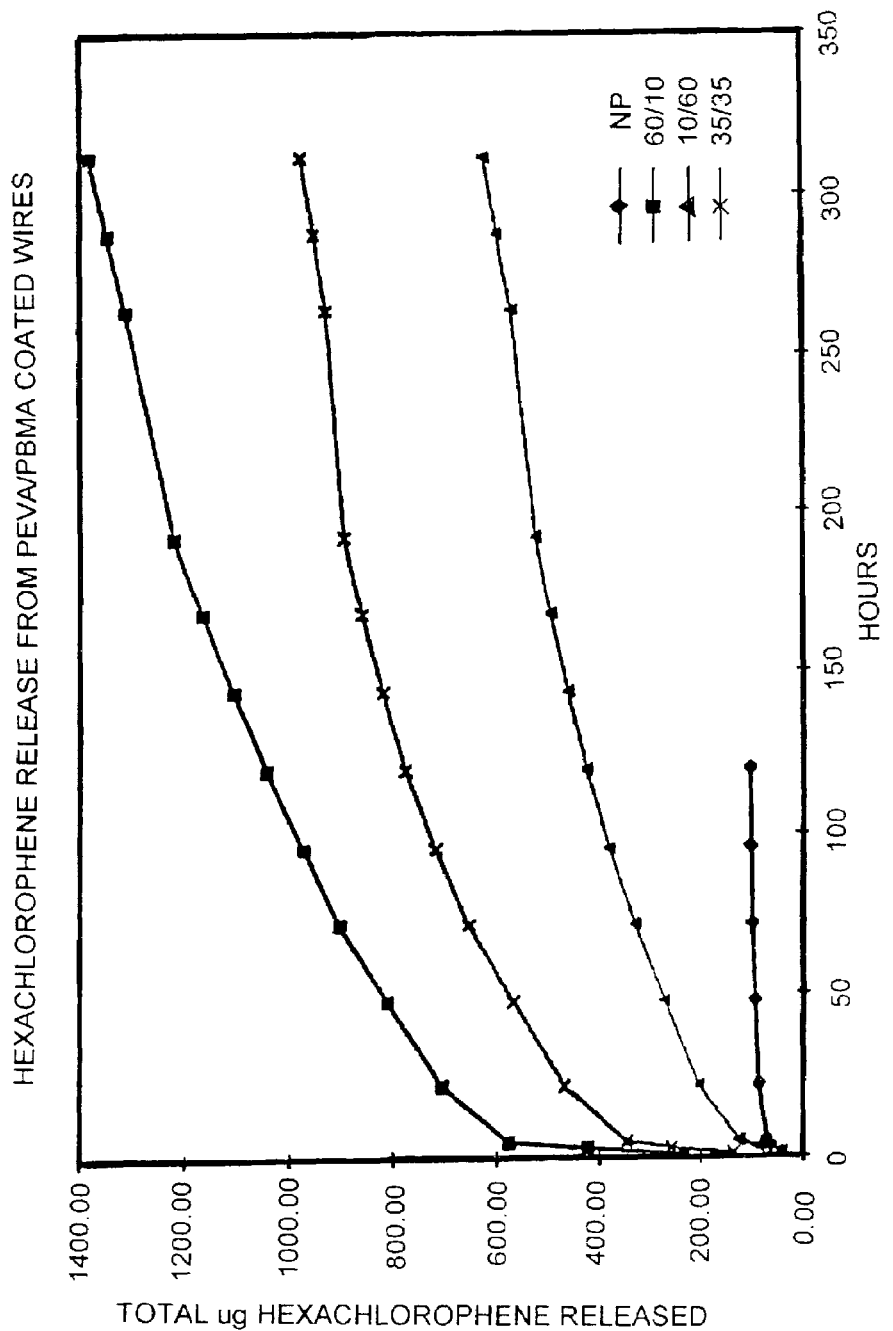
FIG. 1 provides a plot showing the cumulative release profiles for wires coated with compositions according to the present invention, as described in Example 1.

The present invention provides a coating composition and related method for using the composition to coat an implantable medical device with a bioactive agent in a manner that permits the surface to release the bioactive agent over time when implanted in vivo. In a particularly preferred embodiment, the device is one that undergoes flexion and/or expansion in the course of implantation or use in vivo.

The composition comprises a bioactive agent in combination with a plurality of polymers, including a first polymer component and a second polymer component. The polymer components are adapted to be mixed to provide a mixture that exhibits an optimal combination of physical characteristics (e.g., adherence, durability, flexibility) and bioactive release characteristics as compared to the polymers when used alone or in admixture with other polymers previously known. In a preferred embodiment the composition comprises at least one poly(alkyl)(meth)acrylate, as a first polymeric component and poly(ethylene-co-vinyl acetate) ("pEVA") as a second polymeric component.

The composition and method can be used to control the amount and rate of bioactive agent (e.g., drug) release from one or more surfaces of implantable medical devices. In a preferred embodiment, the method employs a mixture of hydrophobic polymers in combination with one or more bioactive agents, such as a pharmaceutical agent, such that the amount and rate of release of agent(s) from the medical device can be controlled, e.g., by adjusting the relative types and/or concentrations of hydrophobic polymers in the mixture. For a given combination of polymers, for instance, this approach permits the release rate to be adjusted and controlled by simply adjusting the relative concentrations of the polymers in the coating mixture. This obviates the need to control the bioactive release rate by polymer selection, multiple coats, or layering of coats, and thus greatly simplifies the manufacture of bioactive-releasing implantable medical devices.

A preferred coating of this invention includes a mixture of two or more polymers having complementary physical characteristics, and a pharmaceutical agent or agents applied to the surface of an implantable medical device which undergoes flexion and/or expansion upon implantation or use. The applied coating is cured (e.g., solvent evaporated) to provide a tenacious and flexible bioactive-releasing coating on the surface of the medical device. The complementary polymers are selected such that a broad range of relative polymer concentrations can be used without detrimentally affecting the desirable physical characteristics of the polymers. By use of the polymer mixtures of the invention the bioactive release rate from a coated medical device can be manipulated by adjusting the relative concentrations of the polymers. Similarly, a spectrum of pharmaceutical agents can be delivered from the coating without the need to find a new polymer or layering the coating on the device.

DETAILED DESCRIPTION OF THE INVENTION

The present invention relates to a coating composition and related method for coating an implantable medical device which undergoes flexion and/or expansion upon implantation. The structure and composition of the underlying device can be of any suitable, and medically acceptable, design and can be made of any suitable material that is compatible with the coating itself. The surface of the medical device is provided with a coating containing one or more bioactive agents.

In order to provide a preferred coating, a composition is prepared to include a solvent, a combination of complementary polymers dissolved in the solvent, and the bioactive agent or agents dispersed in the polymer/solvent mixture. The solvent is preferably one in which the polymers form a true solution. The pharmaceutical agent itself may either be soluble in the solvent or form a dispersion throughout the solvent.

The resultant composition can be applied to the device in any suitable fashion, e.g., it can be applied directly to the surface of the medical device, or alternatively, to the surface of a surface-modified medical device, by dipping, spraying, or any conventional technique. The method of applying the coating composition to the device is typically governed by the geometry of the device and other process considerations. The coating is subsequently cured by evaporation of the solvent. The curing process can be performed at room temperature, elevated temperature, or with the assistance of vacuum.

The polymer mixture for use in this invention is preferably biocompatible, e.g., such that it results in no induction of inflammation or irritation when implanted. In addition, the polymer combination must be useful under a broad spectrum of both absolute concentrations and relative concentrations of the polymers. This means that the physical characteristics of the coating, such as tenacity, durability, flexibility and expandability, will typically be adequate over a broad range of polymer concentrations. Furthermore, the ability of the coating to control the release rates of a variety of pharmaceutical agents can preferably be manipulated by varying the absolute and relative concentrations of the polymers.

A first polymer component of this invention provides an optimal combination of various structural/functional properties, including hydrophobicity, durability, bioactive agent release characteristics, biocompatability, molecular weight, and availability (and cost).

Examples of suitable first polymers include poly(alkyl) (meth)acrylates, and in particular, those with alkyl chain lengths from 2 to 8 carbons, and with molecular weights from 50 kilodaltons to 900 kilodaltons. An example of a particularly preferred first polymer is poly n-butylmethacrylate. Such polymers are available commercially, e.g., from Aldrich, with molecular weights ranging from about 200,000 daltons to about 320,000 daltons, and with varying inherent viscosity, solubility, and form (e.g., as crystals or powder).

A second polymer component of this invention provides an optimal combination of similar properties, and particularly when used in admixture with the first polymer component. Examples of suitable second polymers are available commercially and include poly(ethylene-co-vinyl acetate) having vinyl acetate concentrations of between about 10% and about 50%, in the form of beads, pellets, granules, etc. (commercially available are 12%, 14%, 18%, 25%, 33%). pEVA co-polymers with lower percent vinyl acetate become increasingly insoluble in typical solvents, whereas those with higher percent vinyl acetate become decreasingly durable.

A particularly preferred polymer mixture for use in this invention includes mixtures of poly(butylmethacrylate) (pBMA) and poly(ethylene-co-vinyl acetate) co-polymers (pEVA). This mixture of polymers has proven useful with absolute polymer concentrations (i.e., the total combined concentrations of both polymers in the coating composition), of between about 0.25 and about 70 percent (by weight). It has furthermore proven effective with individual polymer concentrations in the coating solution of between about 0.05 and about 70 weight percent. In one preferred embodiment the polymer mixture includes poly(n-butylmethacrylate) (PBMA) with a molecular weight of from 100 kilodaltons to 900 kilodaltons and a pEVA copolymer with a vinyl acetate content of from 24 to 36 weight percent. In a particularly preferred embodiment the polymer mixture includes poly(n-butylmethacrylate) with a molecular weight of from 200 kilodaltons to 400 kilodaltons and a pEVA copolymer with a vinyl acetate content of from 30 to 34 weight percent. The concentration of the bioactive agent or agents dissolved or suspended in the coating mixture can range from 0.01 to 90 percent, by weight, based on the weight of the final coating composition.

The bioactive (e.g., pharmaceutical) agents useful in the present invention include virtually any therapeutic substance which possesses desirable therapeutic characteristics for application to the implant site. These agents include: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

A coating composition of this invention is preferably used to coat an implantable medical device that undergoes flexion or expansion in the course of its implantation or use in vivo. The words "flexion" and "expansion" as used herein with regard to implantable devices will refer to a device, or portion thereof, that is bent (e.g., by at least 45 degrees or more) and/or expanded (e.g., to more than twice its initial dimension), either in the course of its placement, or thereafter in the course of its use in vivo.

Examples of suitable catheters include urinary catheters, which would benefit from the incorporation of antimicrobial agents (e.g., antibiotics such as vancomycin or norfloxacin) into a surface coating, and intravenous catheters which would benefit from antimicrobial agents and or from antithrombotic agents (e.g., heparin, hirudin, coumadin). Such catheters are typically fabricated from such materials as silicone rubber, polyurethane, latex and polyvinylchloride.

The coating composition can also be used to coat stents, e.g., either self-expanding stents (such as the Wallstent variety), or balloon-expandable stents (as are available in a variety of styles, for instance, Gianturco-Roubin, Palmaz-Shatz, Wiktor, Strecker, ACS Multi-Link, Cordis, AVE Micro Stent), which are typically prepared from materials such as stainless steel or tantalum.

A coating composition of the present invention can be used to coat an implant surface using any suitable means, e.g., by dipping, spraying and the like. The suitability of the coating composition for use on a particular material, and in turn, the suitability of the coated composition can be evaluated by those skilled in the art, given the present description.

The overall weight of the coating upon the surface is typically not important. The weight of the coating attributable to the bioactive agent is preferably in the range of about 0.05 mg to about 10 mg of bioactive agent per $cm^2$ of the gross surface area of the device. More preferably, the weight of the coating attributable to the bioactive is between about 1 mg and about 5 mg of bioactive agent per $cm^2$ of the gross surface area of the device. This quantity of drug is generally required to provide adequate activity under physiological conditions.

In turn, the coating thickness of a presently preferred composition will typically be in the range of about 5 micrometers to about 100 micrometers. This level of coating thickness is generally required to provide an adequate density of drug to provide adequate activity under physiological conditions.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by the embodiments described by the language of the claims and the equivalents of those embodiments. Unless otherwise indicated, all percentages are by weight.

EXAMPLES

Test Methods

The potential suitability of particular coated compositions for in vivo use can be determined by a variety of methods, including the Durability, Flexibility and Release Tests, examples of each of which are described herein.

Sample Preparation

One millimeter diameter stainless steel wires (e.g. 304 grade) are cut into 5 centimeter lengths. The wire segments can be Parylene treated or evaluated with no treatment. The wire segments are weighed on a micro-balance.

Bioactive agent/polymer mixtures are prepared at a range of concentrations in an appropriate solvent, in the manner described herein. The coating mixtures are applied to respective wires, or portions thereof, by dipping or spraying, and the coated wires are allowed to cure by solvent evaporation. The coated wires are re-weighed. From this weight, the mass of the coating is calculated, which in turn permits the mass of the coated polymer(s) and bioactive agent to be determined. The coating thickness can be measured using any suitable means, e.g., by the use of a microprocessor coating thickness gauge (Minitest 4100).

The Durability and Flexibility of the coated composition can be determined in the following manner.

Durability Test

A suitable Durability Test, involves a method in which a coated specimen (e.g., wire) is subjected to repeated frictional forces intended to simulate the type of wear the sample would be exposed to in actual use, such as an implantable device undergoing flexion and/or expansion in the course of its implantation or use.

The Test described below employs a repetitive 60 cycle treatment, and is used to determine whether there is any change in force measurements between the first 5 cycles and the last 5 cycles, or whether there is any observable flaking or scarring detectable by scanning electron microscopy ("SEM") analysis. Regenerated cellulose membrane is hydrated and wrapped around a 200 gram stainless steel sled. The cellulose membrane is clipped tightly on the opposite side of the sled. The sled with rotatable arm is then attached to a 250 gram digital force gauge with computer interface. The testing surface is mounted on a rail table with micro-stepper motor control. The wires are clamped onto the test surface. The cellulose covered sled is placed on top of the wires. Initial force measurements are taken as the sled moves at 0.5 cm/sec over a 5 cm section for 5 push/pull cycles. The sled then continues cycling over the coated samples for 50 push/pull cycles at 5 cm/sec to simulate abrasion. The velocity is then reduced to 0.5 cm/sec and the final force measurements are taken over another 5 push/pull cycles.

SEM micrographs are taken of abraded and nonabraded coated wires to evaluate the effects of the abrasion on the coating.

Flexibility Test

A suitable Flexibility Test, in turn, can be used to detect imperfections (when examined by scanning electron microscopy) that develop in the course of flexing of a coated specimen, an in particular, signs of cracking at or near the area of a bend.

A wire specimen is obtained and coated in the manner described above. One end of the coated wire (1.0 cm) is clamped in a bench vice. The free end of the wire (1.0 cm) is held with a pliers. The wire is bent until the angle it forms with itself is less than 90 degrees. The wire is removed from the vice and examined by SEM to determine the effect of the bending on the coating.

Bioactive Agent Release Assay

A suitable Bioactive Agent Release Assay, as described herein, can be used to determine the extent and rate of drug release under physiological conditions. In general it is desirable that less than 50% of the total quantity of the drug released, be released in the first 24 hours. It is frequently desirable for quantities of drug to be released for a duration of at least 30 days. After all the drug has been released, SEM evaluation should reveal a coherent and defect free coating.

Each coated wire is placed in a test tube with 5 mls of PBS. The tubes are placed on a rack in an environmental orbital shaker and agitated at 37° C. At timed intervals, the PBS is removed from the tube and replaced with fresh PBS. The drug concentration in each PBS sample is determined using the appropriate method.

After all measurable drug has been released from the coated wire, the wire is washed with water, dried, re-weighed, the coating thickness re-measured, and the coating quality examined by SEM analysis.

Example 1

Release of Hexachlorophene from Coated Stainless Steel Wires A one millimeter diameter stainless steel wire (304 grade) was cut into two centimeter segments. The segments were treated with Parylene C coating composition (Parylene is a trademark of the Union Carbide Corporation). This treatment deposits a thin, conformal, polymeric coating on the wires.

Four solutions were prepared for use in coating the wires. The solutions included mixtures of: pEVA (33 weight percent vinyl acetate, from Aldrich Chemical Company, Inc.); poly(butyl methacrylate "pBMA") (337,000 average molecular weight, from Aldrich Chemical Company, Inc.); and hexachlorophene ("HCP") from Sigma Chemical Co., dissolved in tetrahydrofuran. The solutions were prepared as follows:
1) 10 mg/ml pEVA//60 mg/ml pBMA//100 mg/ml HCP
2) 35 mg/ml pEVA//35 mg/ml pBMA//100 mg/ml HCP
3) 60 mg/ml pEVA//10 mg/ml pBMA//100 mg/ml HCP
4) 0 mg/ml pEVA//0 mg/ml pBMA//100 mg/ml HCP Nine wire segments were coated with each coating solution. The following protocol was followed for coating the wire segments. The Parylene-treated wire segments were wiped with an isopropyl alcohol dampened tissue prior to coating. The wire segments were dipped into the coating solution using a 2 cm/second dip speed. The wire segments were immediately withdrawn from the coating solution at a rate of 1 cm/second, after which the coated segments were air-dried at room temperature.

Individual wire segments were placed in tubes containing 2 ml of phosphate buffered saline ("PBS", pH 7.4). The tubes were incubated at 37 degrees centigrade on an environmental, orbital shaker at 100 rotations/minute. The PBS was changed at 1 hour, 3 hours, and 5 hours on the first day, and daily thereafter. The PBS samples were analyzed for HCP concentration by measuring the absorbance of the samples at 298 nms on a UV/visible light spectrophotometer and comparing to an HCP standard curve.

Results are provided in FIG. 1, which demonstrates the ability to control the elution rate of a pharmaceutical agent from a coated surface by varying the relative concentrations of a polymer mixture described by this invention.

Example 2

The polymers described in this disclosure have been evaluated using an Assay protocol as outlined above. The polymer mixtures evaluated have ranged from 100% pBMA to 100% pEVA. Representative results of those evaluations are summarized below.

Control coatings that are made up entirely of pBMA are very durable showing no signs of wear in the Durability Test. When subjected to the Flexibility Test, however, these coatings develop cracks, particularly in the presence of significant concentrations of drug. These coatings also release drug very slowly.

Control coatings that are made up entirely of pEVA, in contrast, are less durable and show no signs of cracking in the Flexibility Test, but develop significant scarring in the Durability Test. These coatings release drugs relatively rapidly, usually releasing more than 50% of the total within 24 hours.

Coatings of the present invention, which contain a mixture of both polymers, are very durable, with no signs of wear in the Durability Test and no cracking in the Flexibility Test. Drug release from these coatings can be manipulated by varying the relative concentrations of the polymers. For instance, the rate of drug release can be controllably increased by increasing the relative concentration of pEVA.

Bioactive agent containing coatings which show no signs of scarring in the Durability Test and no cracking in the Flexibility Test possess the characteristics necessary for application to implantable medical devices that undergo flexion and/or expansion in the course of implantation and/or use.

What is claimed is:

1. A composition for coating the surface of a medical device with one or more bioactive agents in a manner that permits the coated surface to release the bioactive agent(s) over time when implanted in vivo, the composition comprising one or more bioactive agents in combination with a first polymer component comprising at least one poly(alkyl)(meth)acrylate and a second polymer component comprising poly(ethylene-co-vinyl acetate), wherein the device is one that undergoes flexion and/or expansion in the course of implantation or use in vivo.

2. A composition for coating the surface of a medical device with one or more bioactive agents in a manner that permits the coated surface to release the bioactive agent(s) over time when implanted in vivo, the composition comprising one or more bioactive agents in combination with a first polymer component comprising at least one poly(alkyl)(meth)acrylate and a second polymer component comprising poly(ethylene-co-vinyl acetate), wherein the composition permits the amount and rate of release of agent(s) from the medical device to be controlled by adjusting the relative types and/or concentrations of polymers in the mixture.

3. A composition for coating the surface of a medical device with one or more bioactive agent(s) in a manner that permits the coated surface to release the bioactive agent(s) over time when implanted in vivo, the composition comprising one or more bioactive agent(s) in combination with a first polymer component comprising at least one poly(alkyl)(meth)acrylate and a second polymer component comprising poly(ethylene-co-vinyl acetate), wherein the device is selected from the group consisting of catheters and stents.

4. A composition according to claim 1, 2 or 3 wherein the bioactive agent is selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, and gene therapy agents.

5. A composition according to claim 1, 2, or 3 wherein the first and second polymer components are adapted to be mixed to provide a mixture that exhibits an optimal combination of physical characteristics and bioactive release characteristics as compared to the polymers when used alone.

6. A composition according to claim 1, 2, or 3 wherein the amount and rate of release of agent(s) from the medical device can be controlled by adjusting the relative types and/or concentrations of the first polymer component and the second polymer component.

7. A polymeric coating composition comprising a first polymer component comprising at least one poly(alkyl)(meth)acrylate and a second polymer component comprising poly(ethylene-co-vinyl acetate) and one or more bioactive agents and positioned upon the surface of a medical device in a manner that permits the coated surface to release the bioactive agent(s) over time when implanted in vivo, wherein the composition provides sufficient durability and flexibility to be used upon a device is one that undergoes flexion and/or expansion in the course of implantation or use in vivo.

8. A composition according to claim 7 wherein the bioactive release rate from a coated medical device can be manipulated by adjusting the relative concentrations of the first and second polymers.

9. A polymeric coating composition according to claim 7 wherein the coating comprises multiple polymeric layers.

10. A method for providing an implantable medical device with a therapeutic effect, the method comprising the step of providing a medical device having a surface coated with a composition comprising one or more bioactive agents in a manner that permits the coated surface to release the bioactive agent(s) over time when implanted in vivo, the composition comprising one or more bioactive agents in combination with a first polymer component comprising at least one poly(alkyl)(meth)acrylate and a second polymer component comprising poly(ethylene-co-vinyl acetate), wherein the device is one that undergoes flexion and/or expansion in the course of implantation or use in vivo.

11. A method for providing an implantable medical device with a therapeutic effect, the method comprising the step of providing a medical device having a surface of the medical device with a composition comprising one or more bioactive agents in a manner that permits the coated surface to release the bioactive agent(s) over time when implanted in vivo, the composition comprising one or more bioactive agents in combination with a first polymer component comprising at least one poly(alkyl)(meth)acrylate and a second polymer component comprising poly(ethylene-co-vinyl acetate), wherein the composition permits the amount and rate of release of agent(s) from the medical device to be controlled by adjusting the relative types and/or concentrations of polymers in the mixture.

12. A method for providing an implantable medical device with a therapeutic effect, the method comprising the step of providing a medical device having a coated with a composition comprising one or more bioactive agent(s) in a manner that permits the coated surface to release the bioactive agent(s) over time when implanted in vivo, the composition comprising one or more bioactive agent(s) in combination with a first polymer component comprising at least one poly(alkyl)(meth)acrylate and a second polymer component comprising poly(ethylene-co-vinyl acetate), wherein the device is selected from the group consisting of catheters and stents.

13. A method according to claim 10, 11 or 12 wherein the bioactive agent is selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, and gene therapy agents.

14. A method according to claim 10, 11, or 12 wherein the first and second polymer components are adapted to be mixed to provide a mixture that exhibits an optimal combination of physical characteristics and bioactive release characteristics as compared to the polymers when used alone.

15. A method according to claim 10, 11, or 12 wherein the amount and rate of release of agent(s) from the medical device can be controlled by adjusting the relative types and/or concentrations of the first and second polymers.

16. A composition for coating the surface of a medical device with a bioactive agent in a manner that permits the coated surface to release the bioactive agent over time when implanted in vivo, the composition comprising a bioactive agent in combination with a plurality of polymers, including a first polymer component comprising at least one poly(alkyl)(meth)acrylate and a second polymer component comprising poly(ethylene-co-vinyl acetate).

17. A composition according to claim 7 or 16 wherein the bioactive agent comprises an antithrombogenic agent.

18. A composition according to claim 7 or 16 wherein the bioactive agent comprises an anti-inflammatory agent.

19. A composition according to claim 7 or 16 wherein the bioactive agent comprises a remodeling inhibitor.

20. A composition according to claim 7 or 16 wherein the bioactive agent comprises an antiproliferative.

21. A combination comprising a medical device coated with a composition according to claim 7 or 16.

22. A combination according to claim 21 wherein the medical device comprises a stent.

23. A combination according to claim 21 wherein the bioactive agent is selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, and gene therapy agents.

24. A combination according to claim 21 or 22 wherein the bioactive agent comprises an antithrombogenic agent.

25. A combination according to claim 21 or 22 wherein the bioactive agent comprises an anti-inflammatory agent.

26. A composition according to claim 21 or 22 wherein the bioactive agent comprises a remodeling inhibitor.

27. A composition according to claim 21 or 22 wherein the bioactive agent comprises an antiproliferative.

* * * * *